United States Patent
Haick et al.

(10) Patent No.: US 8,945,935 B2
(45) Date of Patent: Feb. 3, 2015

(54) DIAGNOSING, PROGNOSING AND MONITORING MULTIPLE SCLEROSIS

(75) Inventors: Hossam Haick, Haifa (IL); Ariel Miller, Haifa (IL)

(73) Assignees: Technion Research & Development Foundation Ltd., Haifa (IL); Mor Research Applications Ltd., Tel Aviv (IL); Rappaport Family Institute for Research in the Medical Sciences, Haifa (IL)

( * ) Notice: Subject to any disclaimer, the term of this patent is extended or adjusted under 35 U.S.C. 154(b) by 255 days.

(21) Appl. No.: 13/563,812

(22) Filed: Aug. 1, 2012

(65) Prior Publication Data

US 2013/0034910 A1    Feb. 7, 2013

Related U.S. Application Data

(60) Provisional application No. 61/514,911, filed on Aug. 4, 2011.

(51) Int. Cl.

| | | |
|---|---|---|
| *G01N 33/564* | (2006.01) | |
| *G01N 33/497* | (2006.01) | |
| *B82Y 15/00* | (2011.01) | |
| *G01N 33/00* | (2006.01) | |
| G01N 27/12 | (2006.01) | |
| G01N 27/414 | (2006.01) | |

(52) U.S. Cl.
CPC ............. *G01N 33/564* (2013.01); *B82Y 15/00* (2013.01); *G01N 33/497* (2013.01); *G01N 2800/285* (2013.01); *G01N 27/127* (2013.01); *G01N 27/4145* (2013.01); *G01N 27/4146* (2013.01)
USPC .......................................... 436/128; 436/127

(58) Field of Classification Search
CPC ... G01N 33/564; G01N 33/497; G01N 33/53; G01N 33/50; G01N 33/483; G01N 33/48; G01N 33/00; B82Y 15/00
USPC ................................................. 436/128, 127
See application file for complete search history.

(56) References Cited

U.S. PATENT DOCUMENTS

2006/0160134 A1* 7/2006 Melker et al. ................. 435/7.1
2011/0045523 A1* 2/2011 Strano et al. ................... 435/29

FOREIGN PATENT DOCUMENTS

| WO | 2004/065404 | 8/2004 |
|---|---|---|
| WO | 2004/090534 | 10/2004 |
| WO | 2005/027733 | 3/2005 |
| WO | 2007/041245 | 4/2007 |
| WO | 2007/086986 | 8/2007 |
| WO | 2009/066293 | 5/2009 |
| WO | 2009/144725 | 12/2009 |
| WO | 2010/064239 | 6/2010 |
| WO | 2010/079490 | 7/2010 |
| WO | 2010/113096 | 10/2010 |

OTHER PUBLICATIONS

STIC Search Report for U.S. Appl. No. 13/863,812. Conducted by the United States Patent and Trademark Office.*
Bitsch, Andreas and Bruck, Wolfgang (2002) Differentiation of Multiple Sclerosis Subtypes: Implications for Treatment. CNS Drugs 16(6):405-418.
Brust, Mathias et al., (1994) Synthesis of thiol-derivatised gold nanoparticles in a two-phase Liquid-Liquid system . J Chem Soc Chem Commun 1994(7):801-802.
Coelho, Leiliane et al., (2007) Breath air analysis and its use as a biomarker in biological monitoring of occupational and environmental exposure to chemical agents. J Chromatography B 853(1-2):1-9.
Hostetler, Michael J. et al., (1998) Alkanethiolate Gold Cluster Molecules with Core Diameters from 1.5 to 5.2 nm: Core and Monolayer Properties as a Function of Core Size. Langmuir 14(1):17-30.
Link, H. and Huang, Y. M. (2006) Oligoclonal bands in multiple sclerosis cerebrospinal fluid: an update on methodology and clinical usefulness. J Neuroimmunol 180(1-2):17-28.
Ouyang, Gangfeng and Pawliszyn, Janusz (2006) SPME in environmental analysis. Anal Bioanal Chem 386(4):1059-1073.
Peng, G. et al., (2010) Detection of lung, breast, colorectal, and prostate cancers from exhaled breath using a single array of nanosensors. Br J Cancer 103(4):542-551.
Zhao, Xiao-Mei et al., (1997) Soft lithographic methods for nanofabrication. J Mater Chem 7(7):1069-1073.
Zilberman, Yael et al., (2011) Nanoarray of polycyclic aromatic hydrocarbons and carbon nanotubes for accurate and predictive detection in real-world environmental humidity. ACS Nano 5(8):6743-6753.

* cited by examiner

*Primary Examiner* — Christine T Mui
(74) *Attorney, Agent, or Firm* — Roach Brown McCarthy & Gruber, P.C.; Kevin D. McCarthy (57) ABSTRACT

The present invention provides a system and method for diagnosing, monitoring or prognosing Multiple Sclerosis at different stages as well as affording the prediction of disease activity and response to a treatment regimen, using at least one sensor comprising carbon nanotubes or metal nanoparticles, each coated with various organic coatings in conjunction with a pattern recognition algorithm.

20 Claims, 3 Drawing Sheets

Figure 3

DIAGNOSING, PROGNOSING AND MONITORING MULTIPLE SCLEROSIS

REFERENCE TO CO-PENDING APPLICATION

This application claims priority to U.S. provisional patent application Ser. No. 61/514,911, filed on Aug. 4, 2011.

FIELD OF THE INVENTION

The present invention relates to a system and methods for the diagnosis, prognosis or monitoring of Multiple Sclerosis through breath analysis, or for predicting the course of the disease or a patient's response to various treatment regimens.

BACKGROUND OF THE INVENTION

Multiple sclerosis (MS) is a chronic inflammatory disease of the central nervous system (CNS) which occurs at young adults, more prevalent in women than in men. The etiology of MS is unknown, but it is thought to result from a combination of genetic and environmental factors. MS affects the ability of nerve cells in the brain and spinal cord to communicate with each other and control body functions. The clinical disability is linked to an inflammation of the myelin, the protective sheath around the axons of the central nervous system (CNS), which is damaged due to an autoimmune attack and neurodegenerative processes. As a consequence, the white matter of the brain and spinal cord becomes scarred by focal lesions (plaques) leading to progressive neurological dysfunction including demyelination and neurodegeneration.

Currently, there is no specific test for diagnosing MS and the diagnosis relies on the recognition of the clinical history of the subject. Clinical data which includes various episodes of neurologic symptoms, especially in young adults, suggests the diagnosis of MS. In many instances the diagnosis can be supported by the analysis of the cerebrospinal fluid (CSF) and evoked potential (EP) studies of the visual, auditory and somatosensory pathway, as well as by recently applied techniques of Magnetic Resonance Imaging (MRI) of the brain and spinal cord. These techniques, however, suffer from several disadvantages. For example, the analysis of the CSF is performed by electrophoresis for detecting oligoclonal bands (OCB) of IgG, which is a biomarker present in 75-85% of individuals having MS and can provide evidence of chronic inflammation of the central nervous system (Link et al., J. Neuroimmunol., 180(1-2), 17-28, 2006). However, OCB are often non-detectable at the early stages of MS thereby leading to false negative results. The extraction of the cerebrospinal fluid involves an invasive lumbar puncture procedure that can cause a major discomfort to the subject with accompanying symptoms including dizziness, severe headache, etc. MRI is an expensive procedure which requires the injection of a contrast material (gadolinium) prior to performing the scan. Additionally, MRI cannot provide information about the pathological composition of the lesions.

Multiple sclerosis may progress and regress unpredictably. However, there are several patterns of symptoms. Approximately 85-90% of patients experience a relapsing-remitting (RRMS) course at the initial stage which then becomes progressive (PMS) in 40% of the patients. Progressive MS can be sub-classified into primary progressive course (PPMS) and secondary progressive course (SPMS). The different MS subtypes are characterized by the past course of the disease (e.g. unpredictable relapses, remissions and progression of neurologic decline). From a clinical perspective, patients with different disease courses show different responses to treatment. For instance, patients with RRMS are more likely to respond to immunomodulatory therapy than those with a progressive disease course (Bitsch et al., CNS Drugs, 16(6), 405-418, 2002). Thus, characterizing the MS subtype is important not only for prognosis but also for disease management. Moreover, early detection of MS is extremely important to allow early onset of treatment that could significantly slow down the progression of the disease and related accumulating disability as well as improve health-related quality of life.

Biomarkers are anatomic, physiologic, biochemical or molecular parameters associated with specific disease states. The search for MS biomarkers has been focused on indicators of the general activity of the inflammatory process as well as its consequences such us neurodegeneration and axonal loss. Several biomarkers and methods of use thereof in diagnosing MS are disclosed in e.g. WO 2010/113096, WO 2007/041245, and WO 2005/027733. However, most of the MS biomarkers are CSF or serum derived thus necessitating the performance of invasive tests, which limit the possibilities of repeated measurements as part of long-term follow-up, as required in these chronic patients.

WO 2004/065404 discloses a method for detecting a target analyte/biomarker in exhaled breath comprising a) exposing the exhaled breath an aptamer capable of selectively binding to the target analyte/biomarker, wherein the aptamer is linked with a molecular beacon; and b) detecting a signal generated by the molecular beacon.

WO 2007/086986 discloses a method for detecting a target analyte/biomarker in exhaled breath comprising: a) exposing to the exhaled breath a molecular recognition agent capable of selectively binding to the target analyte/biomarker, wherein the molecular recognition agent is linked with a signaling agent; and b) detecting a signal generated by the signaling agent.

WO 2004/065404 and WO 2007/086986 further disclose a method for screening analytes/biomarkers which method includes providing blood specimens from patients with known diseases (i.e., Alzheimer's disease, multiple sclerosis) and screening the specimens for the presence of biomarkers in blood components and exhaled breath.

WO 2004/090534 discloses a non-invasive breath analysis using Field Asymmetric Ion Mobility Spectrometry (FAIM) for the detection of several disorders. Specifically, FAIM spectrometers are suggested as being useful for analyzing the presence of pentane in a patient sample, for example a breath sample, which provides a marker for arthritis and multiple sclerosis.

WO 2009/144725 to one of the inventors of the present application discloses a system for detecting volatile organic compounds derived from a breath sample, the system comprising: (a) an apparatus comprising an array of chemically sensitive sensors of single walled carbon nanotubes coated with non-polar small organic molecules, and (b) a processing unit comprising a learning and pattern recognition analyzer wherein the learning and pattern recognition analyzer receives sensor output signals and compares them to stored data.

WO 2010/064239 to one of the inventors of the present application discloses a system comprising an array of sensors for measuring volatile organic compounds as biomarkers for diagnosis, prognosis and monitoring of renal insufficiencies, the system comprises an array of sensors comprising a (semi-) conductive random network of single-walled carbon nanotubes (SWCNTs) coated with an organic coating which comprises oligomers or polymers modified with at least one polar functional group, in conjunction with learning and pattern recognition algorithms.

WO 2009/066293 to one of the inventors of the present application discloses an apparatus comprising at least one chemically sensitive sensor for detecting volatile and non-volatile compounds, wherein the chemically sensitive sensor comprises cubic nanoparticle conductive cores capped with an organic coating. Methods of use thereof in identifying various disease biomarkers, and in food quality and environmental control are disclosed.

WO 2010/079490 to one of the inventors of the present application discloses a sensor array for detecting biomarkers for cancer in breath samples. The sensor array is based on 2D films or 3D assemblies of conductive nanoparticles capped with an organic coating wherein the nanoparticles are characterized by a narrow size distribution.

There remains an unmet need for a non-invasive and cost-effective technique for confirming the diagnosis of Multiple Sclerosis, distinguishing the disease specific subtypes (relapsing-remitting vs. progressive Multiple Sclerosis), assessment of disease activity (predicting relapse vs. remission) and prognosis as well as the assessment and prediction of response to therapeutics in patients with MS.

SUMMARY OF THE INVENTION

The present invention provides a system and methods for diagnosing, monitoring or prognosing MS in a subject. The system and methods of the present invention further provide the differentiation between disease states, namely relapse vs. remission in MS, the assessment or prediction of the course of the disease as well as the prediction of the response to a treatment regimen.

The system and methods of the present invention provide the diagnosis, prognosis or monitoring of MS at its various stages, including differentiation between healthy subjects and subjects having MS at its various stages. The present invention is based in part on the unexpected finding that a sensor array comprising at least one sensor comprising a random network of carbon nanotubes coated with a first organic coating and/or a film/assembly of metal nanoparticles coated with a second organic coating provides sensitivity and selectivity for volatile biomarkers in breath samples which are indicative of MS. The use of the sensor array in conjunction with a pattern recognition algorithm further provides information regarding the subtype of MS thus allowing a comprehensive MS management, including monitoring of disease progression and treatment.

According to one aspect, the present invention provides a system for diagnosing, monitoring or prognosing Multiple Sclerosis or stages thereof, or predicting the course of the disease or a patient's response to a treatment regimen, the system comprising: (a) an apparatus comprising at least one sensor comprising nanomaterials selected from single walled carbon nanotubes coated with a first organic coating, metal nanoparticles coated with a second organic coating, and a combination thereof; (b) a detection means; and (c) a processing unit comprising a pattern recognition analyzer, wherein the pattern recognition analyzer receives sensor output signals and compares them to stored data so as to enable the diagnosis, monitoring or prognosis of Multiple Sclerosis or stages thereof, or the prediction of the course of the disease or a patient's response to a treatment regimen.

In one embodiment, the apparatus comprises a combination of a sensor comprising a plurality of single walled carbon nanotubes coated with a first organic coating and a sensor comprising a plurality of metal nanoparticles coated with a second organic coating.

In one embodiment, the first organic coating comprises small molecules, oligomers, polymers, or a combination thereof. In some embodiments, the first organic coating comprises molecules selected from unsubstituted or substituted $C_1$-$C_{40}$ linear or branched alkanes, cycloalkanes, aromatic compounds and combinations thereof. Each possibility represents a separate embodiment of the present invention. In certain embodiments, the organic molecules of the first organic coating are substituted by at least one of a carboxyl, an acyl, an ester, a nitro, a halogen, a hydroxyl or a haloalkyl moiety. Each possibility represents a separate embodiment of the present invention. In specific embodiments, the first organic coating comprises compounds selected from the group consisting of propyl gallate ($C_{10}H_{12}O_5$), anthracene ($C_{14}H_{10}$), tetracosanoic acid ($C_{24}H_{48}O_2$), tricosane ($C_{23}H_{48}$), 3-methyl-2-phenyl valeric acid ($C_{12}H_{16}O_2$), tris(hydroxymethyl)nitro-methane ($C_4H_9NO_5$), tetracosane ($C_{24}H_{50}$), dioctyl phthalate ($C_{24}H_{38}O_4$), 1,2,5,6,9,10-hexabrormo-cyclododecane ($C_{12}H_{18}Br_6$), pentadecane ($C_{15}H_{32}$), and combinations thereof. Each possibility represents a separate embodiment of the present invention.

In other embodiments, the first organic coating comprises arenes, polyarenes, or combinations thereof. In certain embodiments, the arenes or polyarenes are selected from the group consisting of naphthalene, acenaphtene, anthracene, phenanthrene, pyrene, benzo[a]pyrene, chrysene, fluoranthene, $C_{18}$-$C_{180}$ graphenes and combinations thereof. Each possibility represents a separate embodiment of the present invention. In specific embodiments, the arenes or polyarenes are $C_{18}$-$C_{180}$ graphenes, for example $C_{42}$ graphene, $C_{50}$ graphene and the like.

In certain embodiments, the arenes or polyarenes are substituted with hydrophobic or hydrophilic carbon chains and/or at least one functional group selected from the group consisting of ester, ether, alcohol, amine, imine, amide, ammonium, keto, aldehyde, halogen (halo), pyridyl, phosphate, thiol, sulfonate, sulfonyl, hydroxyl, carboxylate, carboxyl, and carbonate groups. Each possibility represents a separate embodiment of the present invention.

In particular embodiments, the first organic coating comprises hexa-peri-hexabenzocoronene (HBC) molecules, which are unsubstituted or substituted by any one of 2-ethylhexyl (HBC-$C_{6,2}$), 2-hexyldecane (HBC-$C_{10,6}$), 2-decyl tetradecane (HBC-$C_{14,10}$), and dodecane (HBC-$C_{12}$). Each possibility represents a separate embodiment of the present invention.

In another embodiment, the single walled carbon nanotubes are organized in a random network configuration.

In other embodiments, the single walled carbon nanotubes have diameters ranging from about 0.9 nanometer to about 5 nanometers, and lengths ranging from about 1 micrometer to about 50 micrometers.

In further embodiments, the metal nanoparticles are selected from the group consisting of Au, Ag, Ni, Co, Pt, Pd, Cu, Al nanoparticles and combinations thereof. Each possibility represents a separate embodiment of the present invention.

In some embodiments, the second organic coating comprises compounds selected from the group consisting of alkylthiols, arylthiols, alkylarylthiols, alkylthiolates, ω-functionalized alkanethiolates, arenethiolates, (γ-mercaptopropyl)trimethyloxysilane, dialkyl disulfides and combinations and derivatives thereof. Each possibility represents a separate embodiment of the present invention.

In particular embodiments, the second organic coating comprises compounds selected from the group consisting of hexanethiol, decanethiol, octadecanethiol, tert-odecanethiol, 2-mercaptobenzimidazole, 2-ethylhexyl-3-mercaptopropionate and combinations thereof. Each possibility represents a separate embodiment of the present invention.

In other embodiments, the metal nanoparticles have a morphology selected from a cubic, a spherical, and a spheroidal morphology. Each possibility represents a separate embodiment of the present invention.

In certain embodiments, the at least one sensor is configured in a form selected from the group consisting of a capacitive sensor, a resistive sensor, a chemoresistive sensor, an impedance sensor, and a field effect transistor sensor. Each possibility represents a separate embodiment of the present invention.

In some embodiments, the system comprises a single sensor.

In other embodiments, the system comprises a plurality of sensors, for example between 2 and 8 sensors. In additional embodiments, the plurality of sensors comprises at least one sensor comprising single walled carbon nanotubes coated with a first organic coating as described herein and at least one sensor comprising metal nanoparticles coated with a second organic coating as described herein.

In other embodiments, the detection means comprises a device for measuring changes in resistance, conductance, alternating current (AC), frequency, capacitance, impedance, inductance, mobility, electrical potential, optical property or voltage threshold. Each possibility represents a separate embodiment of the present invention.

In further embodiments, the pattern recognition analyzer comprises at least one algorithm selected from the group consisting of artificial neural network algorithms, principal component analysis (PCA), multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART), partial least squares (PLS), multiple linear regression (MLR), principal component regression (PCR), discriminant function analysis (DFA), linear discriminant analysis (LDA), cluster analysis, and nearest neighbor. Each possibility represents a separate embodiment of the present invention. In one embodiment, the at least one algorithm is discriminant function analysis (DFA).

In another aspect, the present invention provides a method of diagnosing, monitoring or prognosing MS or stages thereof in a subject, the method comprising the steps of: (a) providing a system comprising an apparatus comprising at least one sensor comprising nanomaterials selected from single walled carbon nanotubes coated with a first organic coating, metal nanoparticles coated with a second organic coating and a combination thereof; a detection means; and a processing unit comprising a pattern recognition analyzer comprising at least one pattern recognition algorithm; (b) exposing the at least one sensor to a test exhaled breath sample; (c) measuring at least one response induced parameter from the at least one sensor upon exposure to the test sample to obtain a response pattern; and (d) analyzing the response pattern obtained in step (c) using a pattern recognition algorithm by comparing it to stored data obtained from a control sample whereby a significantly different response pattern of the test sample as compared the control sample is indicative of MS or stages thereof.

In some embodiments, the method disclosed herein further enables the differentiation between healthy subjects, subjects having primary progressive multiple sclerosis (PPMS), and subjects having secondary progressive multiple sclerosis (SPMS).

In other embodiments, the method enables the differentiation between healthy subjects, subjects in a relapsing remitting stage of multiple sclerosis (RRMS) and subject in a progressive stage of multiple sclerosis (PMS), which may be a primary progressive stage of MS (PPMS) or secondary progressive stage of MS (SPMS). Each possibility represents a separate embodiment of the present invention.

In further embodiments, the method enables the differentiation between subjects in a relapsing remitting stage of multiple sclerosis (RRMS) at remission and subjects in a relapsing remitting stage of multiple sclerosis (RRMS) at a state of relapse (increased disease activity).

In certain embodiments, the method is directed to monitoring or predicting the course of the disease.

In some embodiments, the method is directed to prognosing or monitoring the treatment of MS, or predicting a patient's response to a treatment regimen.

In another embodiment, the method of the present invention further comprises the step of concentrating the test exhaled breath sample prior to step (b) using at least one of a breath concentrator and a dehumidifying unit.

In certain embodiments, the response pattern is formed by the sensor detection of at least one volatile biomarker which is indicative of MS or stages thereof. In particular embodiments, the at least one volatile biomarker which is indicative of MS or stages thereof is hexanal or 5-methyl-undecane.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

The present invention provides a method of diagnosing, monitoring or prognosing MS using at least one sensor comprising carbon nanotubes coated with organic molecules (e.g. graphenes) and/or at least one sensor comprising metal nanoparticles capped with an organic coating (e.g. mercapto derivatives). The invention further provides a method of distinguishing between healthy subjects, subjects having progressive multiple sclerosis (PMS) and subjects having steady states of multiple sclerosis. Additional embodiments provide the monitoring and prediction of the disease course and the assessment and prediction of responses to various treatments of MS, thus enabling optimized MS management.

The present invention provides a system which is suitable for the diagnosis, monitoring or prognosis of MS at its various stages. In some embodiments, the system is suitable for the prediction and assessment of MS treatments. In other embodiments, the system is suitable for the prediction and assessment of disease activity (exacerbation of the disease, for example relapse episodes). The system includes at least one chemically sensitive sensor as described herein, a detection means and a processing unit which utilizes at least one pattern recognition algorithm to receive sensor output signals and compare them to stored data so as to enable the diagnosis, monitoring or prognosis of MS or stages thereof or the prediction of the course of the disease or a patient's response to a treatment regimen.

A novel approach disclosed herein for the first time overcomes the deficiencies of the currently available MS diagnostic techniques by providing a non-invasive and cost-effective technique for detecting and monitoring MS as well as tailoring therapeutics for the MS patient thus affording personalized MS medicinal care, via the detection of patterns of volatile specific biomarkers in exhaled breath samples.

According to one embodiment, the at least one chemically sensitive sensor comprises single-walled carbon nanotubes (SWCNTs) coated with organic molecules. In some embodiments, the single-walled carbon nanotubes are arranged in a random network configuration. In other embodiments, the network of SWCNTs can be fabricated by a physical manipulation or in a self-assembly process. The term "self-assembly" as used herein refers to a process of the organization of molecules without intervening from an outside source. The self-assembly process occurs in a solution/solvent or directly on a solid-state substrate.

Main approaches for the synthesis of carbon nanotubes in accordance with the present invention include, but are not limited to, laser ablation of carbon, electric arc discharge of graphite rod, and chemical vapor deposition (CVD) of hydrocarbons. Among these approaches, CVD coupled with photolithography has been found to be the most versatile in the preparation of various carbon nanotube devices. In a CVD method, a transition metal catalyst is deposited on a substrate (e.g. silicon wafer) in the desired pattern, which may be fashioned using photolithography followed by etching. The substrate having the catalyst deposits is then placed in a furnace in the presence of a vapor-phase mixture of, for example, xylene and ferrocene. Carbon nanotubes typically grow on the catalyst deposits in a direction which is normal to the substrate surface. Various carbon nanotube materials and devices are now available from commercial sources.

Other CVD methods include the preparation of carbon nanotubes on silica ($SiO_2$) and silicon surfaces without using a transition metal catalyst. Accordingly, areas of silica are patterned on a silicon wafer by photolithography and etching. Carbon nanotubes are then grown on the silica surfaces in a CVD or a plasma-enhanced CVD (PECVD) process. These methods provide the production of carbon nanotube bundles in various shapes.

The term "single walled carbon nanotube" as used herein refers to a cylindrically shaped thin sheet of carbon atoms having a wall which is essentially composed of a single layer of carbon atoms which are organized in a hexagonal crystalline structure with a graphitic type of bonding. A nanotube is characterized by the length-to-diameter ratio. It is to be understood that the term "nanotubes" as used herein refers to structures in the nanometer as well as micrometer range.

According to various embodiments, the single-walled carbon nanotubes of the present invention have diameters ranging from about 0.6 nanometers (nm) to about 100 nm and lengths ranging from about 50 nm to about 10 millimeters (mm) More preferably, the single-walled carbon nanotubes have diameters ranging from about 0.7 nm to about 50 nm and lengths ranging from about 250 nm to about 1 mm. Even more preferably, the single-walled carbon nanotubes have diameters ranging from about 0.8 nm to about 10 nm and lengths ranging from about 0.5 micrometer ($\mu m$) to about 100 $\mu m$. Most preferably, the single-walled carbon nanotubes of the present invention have diameters ranging from about 0.9 nm to about 5 nm and lengths ranging from about 1 $\mu m$ to about 50 $\mu m$.

According to the principles of the present invention, the single walled carbon nanotubes are coated with a first organic coating comprising small molecules, oligomers, polymers or combinations thereof. In some embodiments, the first organic coating comprises molecules including, but not limited to, unsubstituted or substituted $C_1$-$C_{40}$ linear or branched alkanes, cycloalkanes, aromatic compounds, and combinations thereof. Each possibility represents a separate embodiment of the present invention. The molecules may be substituted by at least one of a carboxyl, an acyl, an ester, a nitro, a halogen, a hydroxyl or a haloalkyl moiety. Each possibility represents a separate embodiment of the present invention. Suitable small organic molecules include, but are not limited to, propyl gallate ($C_{10}H_{12}O_5$), anthracene ($C_{14}H_{10}$), tetracosanoic acid ($C_{24}H_{48}O_2$), tricosane ($C_{23}H_{48}$), 3-methyl-2-phenyl valeric acid ($C_{12}H_{16}O_2$), tris(hydroxymethyl)nitromethane ($C_4H_9NO_5$), tetracosane ($C_{24}H_{50}$), dioctyl phthalate ($C_{24}H_{38}O_4$), 1,2,5,6,9,10-hexabrormo-cyclododecane ($C_{12}H_{18}Br_6$), pentadecane ($C_{15}H_{32}$), and combinations thereof. Each possibility represents a separate embodiment of the present invention.

Suitable oligomers or polymers include, but are not limited to, arenes, polyarenes or combinations thereof. As used herein the term "arene" refers to single as well as linked or fused aromatic rings which may be further substituted. The term "polyarene" as used herein refers to polycyclic aromatic hydrocarbons which comprise three or more rings, wherein at least two of which are aromatic and in which at least two of these aromatic rings are fused by sharing two adjacent carbon atoms. Suitable arenes or polyarenes include, but are not limited to, naphthalene, acenaphtene, anthracene, phenanthrene, pyrene, benzo[a]pyrene, chrysene, fluoranthene, $C_{18}$-$C_{180}$ graphenes and combinations thereof. Each possibility represents a separate embodiment of the present invention. The term "arene" further includes heteroarenes wherein one or more ring carbon atoms of the arene is replaced with a heteroatom (e.g., N, S, P or O), for example, phenyl-thiophenyl-phenyl-thiophenyl. Arenes may be non-functionalized (un-substituted) or may be functionalized with one or more substituents, for example hydrophobic or hydrophilic carbon chains. In addition, the arenes or the hydrophoboic or hydrophilic carbon chains may be functionalized with least one functional group including, but not limited to, ester, ether, alcohol, amine, imine, amide, ammonium, keto, aldehyde, halogen (halo), pyridyl, phosphate, thiol, sulfonate, sulfonyl, hydroxyl, carboxylate, carboxyl, and carbonate groups. Each possibility represents a separate embodiment of the present invention.

One class of arenes or polyarenes within the scope of the present invention is $C_{18}$-$C_{180}$ graphenes, for example $C_{42}$ graphene, $C_{50}$ graphene and the like. The term "graphene" as used herein refers to a molecule in which a plurality of carbon atoms (e.g., in the form of five-membered rings, six-membered rings, and/or seven-membered rings) are covalently bound to each other to form a (typically sheet-like) polycyclic aromatic molecule. In one embodiment, the graphene comprises a single layer of carbon atoms that are covalently bound to each other (most typically $sp^2$ bonded). It should be noted that such sheets may have various configurations, and that the particular configuration will depend, inter alia, on the amount and position of five-membered and/or seven-membered rings in the sheet. In another embodiment, the graphene comprises several (e.g., two, three, four, five to ten, one to twenty, one to fifty, or one to hundred) single layers of carbon atoms which are stacked together to a maximum thickness of less than about 100 nanometers.

In various embodiments, the first organic coating comprises hexa-peri-hexabenzocoronene (HBC) molecules, which are unsubstituted or substituted by any one of 2-ethylhexyl (HBC-$C_{6,2}$), 2-hexyldecane (HBC-$C_{10,6}$), 2-decyl tetradecane (HBC-$C_{14,10}$), and dodecane (HBC-$C_{12}$). Each possibility represents a separate embodiment of the present invention.

According to some embodiments, the at least one sensor comprises nanoparticles comprising conductive metal cores which are coated with a second organic coating. Suitable non-limiting examples of conductive metal cores include, but are not limited to, Au, Ag, Ni, Co, Pt, Pd, Cu, Al nanoparticles and combinations thereof. Each possibility represents a separate embodiment of the present invention.

In one embodiment, the conductive nanoparticle cores are coated with a second organic coating which comprises a monolayer or multilayers of organic compounds, wherein the organic compounds can be monomers, oligomers, polymers or a combination thereof. Suitable organic compounds include, but are not limited to, alkylthiols, e.g., alkylthiols with $C_3$-$C_{24}$ chains, arylthiols, alkylarylthiols, alkenyl thiols, alkynyl thiols, cycloalkyl thiols, heterocyclyl thiols, heteroaryl thiols, alkylthiolates, alkenyl thiolates, alkynyl thiolates, cycloalkyl thiolates, heterocyclyl thiolates, heteroaryl thiolates, ω-functionalized alkanethiolates, arenethiolates, (γ-mercaptopropyl)tri-methyloxysilane, dialkyl disulfides and combinations thereof. Each possibility represents a separate embodiment of the present invention. In particular embodiments, the organic coating of the metal nanoparticles comprises 3-mercapto-hexanethiol. In other embodiments, the organic coating of the metal nanoparticles comprises decanethiol. In yet other embodiments, the organic coating of the metal nanoparticles comprises octadecanethiol. In other embodiments, the organic coating of the metal nanoparticles comprises tert-odecanethiol. In further embodiments, the organic coating of the metal nanoparticles comprises 2-mercaptobenzimidazole. In additional embodiments, the organic coating of the metal nanoparticles comprises 2-ethylhexyl-3-mercaptopropionate.

Sensors comprising metal nanoparticles capped with various organic coatings can be synthesized as is known in the art, for example using the two-phase method (Brust et al., J. Chem. Soc. Chem. Commun., 7, 801-802, 1994) with some modifications (Hostetler et al., Langmuir, 14(1), 17-30, 1998). Capped gold nanoparticles can be synthesized by transferring $AuCl_4^-$ from aqueous $HAuCl_4.xH_2O$ solution to a toluene solution by the phase-transfer reagent TOAB. After isolating the organic phase, excess thiols are added to the solution. The mole ratio of thiol: $HAuCl_4.xH_2O$ can vary between 1:1 and 10:1, depending on the thiol used. This is performed in order to prepare mono-disperse solution of gold nanoparticles in an average size of about 3.5-5 nm. Exemplary procedures include, but are not limited to, thiol:Au mole ratios of 10:1 and 1:1 for dodecanethiol and butanethiol-capped gold nanoparticles, respectively at an average size of about 5 nm. After vigorous stirring of the solution, aqueous solution of the reducing agent $NaBH_4$ in large excess is added. The reaction is constantly stirred at room temperature for at least 3 hours to produce a dark brown solution of the thiol-capped Au nanoparticles. The resulting solution is further subjected to solvent removal in a rotary evaporator followed by multiple washings using ethanol and toluene. Gold nanoparticles capped with 2-mercaptobenzimidazole can be synthesized by ligand-exchange method from pre-prepared hexanethiol-capped gold nanoparticles. In a typical reaction, excess of thiol, 2-mercaptobenzimidazole, is added to a solution of hexanethiol-capped gold nanoparticles in toluene. The solution is kept under constant stirring for a few days in order to allow as much ligand conversion as possible. The nanoparticles are purified from free thiol ligands by repeated extractions. The metal nanoparticles may have any desirable morphology including, but not limited to, a cubic, a spherical, and a spheroidal morphology. Each possibility represents a separate embodiment of the present invention.

The synthesized nanoparticles can then be assembled (e.g. by a self-assembly process) to produce a film of capped nanoparticles. The term "film", as used herein, corresponds to a configuration of well-arranged assembly of capped nanoparticles. 2D films or 3D film assemblies (stacked films) of capped nanoparticles may also be used. Exemplary methods for obtaining well-ordered two or three dimensional films/assemblies of capped nanoparticles include, but are not limited to, i. Random deposition from solution of coated nanoparticles on solid surfaces. The deposition is performed by drop casting, spin coating, spray coating and other similar techniques.
ii. Field-enhanced or molecular-interaction-induced deposition from solution of coated nanoparticles on solid surfaces.
iii. Langmuir-Blodgett or Langmuir-Schaefer techniques. The substrate is vertically plunged through self-organized/well-ordered 2D monolayer of coated nanoparticles at the air-subphase interface, wherein the latter is being subsequently transferred onto it. Multiple plunging of the substrate through the 2D monolayer of coated nanoparticles at the air-subphase interface, results in the fabrication of the 3D-ordered multilayers of coated nanoparticles.
iv. Soft lithographic techniques, such as micro-contact printing (mCP), replica molding, micro-molding in capillaries (MIMIC), and micro-transfer molding (mTM). These methods are based on variations of self-assembly and replica molding of organic molecules and polymeric materials, for fabricating coated nanoparticles from nanometer-scale to a mesoscopic scale (Zhao et al., J. Mater. Chem., 7(7), 1069-1074, 1997).
v. Various combinations of Langmuir-Blodgett or Langmuir-Schaefer methods with soft lithographic techniques can be used to produce patterned Langmuir-Blodgett films of molecularly modified coated nanoparticles which are transferred onto solid substrates.
vi. Printing on solid-state or flexible substrates using an inject printer designated for printed electronics. A solution containing coated nanoparticles is used as a filling material (or "ink") of the printing head according to procedures well known in the art.

The sensors of the present invention can be configured as any one of the various types of electronic devices, including, but not limited to, capacitive sensors, resistive sensors, chemiresistive sensors, impedance sensors, field effect transistor sensors, and the like, or combinations thereof. Each possibility represents a separate embodiment of the present invention.

In one embodiment, the system of the present invention comprises a single sensor. In alternative embodiments, the system of the present invention comprises a plurality of sensors (sensor array), for example between 2 and 8 sensors. In some embodiments, the sensor array comprises a sensor of single walled carbon nanotubes coated with organic molecules and/or a sensor of metal nanoparticles capped with an organic coating. In one embodiment, the sensor array comprises a plurality of sensors comprising a combination of sensors of single walled carbon nanotubes coated with organic molecules as defined herein and sensors of metal nanoparticles capped with an organic coating as defined herein.

In certain embodiments, the sensors of the present invention comprise one or more conducting elements. The conducting elements may include a source and a drain electrode separated from one another by a source-drain gap.

The system disclosed herein may further comprise a gate electrode wherein the sensor signal may be indicative of a certain property of the nanomaterial under the influence of a gate voltage. Alternatively, the sensor signal may be indicative of a capacitance property of the nanomaterial.

The sensor signal may be induced, according to the principles of the present invention by a change in any one or more of conductivity, resistance, impedance, capacitance, inductance, or optical properties of the sensors upon exposure to volatile biomarkers. Changes in the optical properties of the sensor(s) can be measured using e.g., spectroscopic ellipsometry.

The sensor signal is detected by a detection means. Suitable detection means include devices which are susceptible to a change in any one or more of resistance, conductance, alternating current (AC), frequency, capacitance, impedance, inductance, mobility, electrical potential, optical property and voltage threshold. Each possibility represents a separate embodiment of the present invention. In additional embodiments, the detection means includes devices which are susceptible to swelling or aggregation of nanomaterials as well as devices which are susceptible to a change in any one or more of optical signal, florescence, chemiluminsence, photophorescence, bending, surface acoustic wave, piezoelectricity and the like. Each possibility represents a separate embodiment of the present invention.

In some embodiments, the sensing signal is obtained through the adsorption of the analyte/volatile biomarker on the nanomaterial. According to the principles of the present invention, the signal is generated by the change in conformation/structure of the nanomaterial upon analyte/volatile biomarker adsorption. The present invention thus provides the direct sensing of the analyte/volatile biomarker thus obviating the need for a signaling agent.

According to another embodiment, the present invention further provides a processing unit comprising a pattern recognition analyzer, wherein the pattern recognition analyzer receives sensor output signals and analyzes them by at least one pattern recognition algorithm to produce an output signature. By comparing an unknown signature with a database of stored or known signatures, volatile biomarkers can be identified. The analyzer utilizes pattern recognition algorithms comprising artificial neural networks, such as multilayer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART) and statistical methods such as principal component analysis (PCA), partial least squares (PLS), multiple linear regression (MLR), principal component regression (PCR), discriminant function analysis (DFA) including linear discriminant analysis (LDA), and cluster analysis including nearest neighbor. Each possibility represents a separate embodiment of the present invention. In an exemplary embodiment, the algorithm used for processing the data is discriminant function analysis (DFA).

Additional algorithms suitable for identifying patterns of volatile biomarkers and quantifying their concentration include, but are not limited to, Fisher linear discriminant analysis (FLDA), soft independent modeling of class analogy (SIMCA), K-nearest neighbors (KNN), neural networks, genetic algorithms, and fuzzy logic algorithms. Each possibility represents a separate embodiment of the present invention. In some embodiments, the Fisher linear discriminant analysis (FLDA) and canonical discriminant analysis (CDA) and combinations thereof are used to compare the output signature and the available data from the database. Other classification techniques may also be employed. After analysis is completed, the resulting information can be displayed on a display or transmitted to a host computer.

The present invention further provides an ex-vivo method of diagnosing, monitoring or prognosing MS or stages thereof in a subject using the system of the present invention. The at least one sensor is exposed to a test exhaled breath sample and at least one response induced parameter is measured by a detection means. The obtained signal is a response pattern which is preferably analyzed using a pattern recognition algorithm by comparing it to stored data obtained from a control sample whereby a significantly different response pattern of the test sample as compared the control sample is indicative of MS or stages thereof. In some embodiments, the present invention provides a method for predicting the course of the disease or the exacerbation of disease activity (e.g. relapse episodes). In other embodiments, the present invention provides a method for assessing and predicting a response of the disease to a therapeutic agent.

The term "significantly different" as used herein refers to a statistically significant quantitative difference between the pattern(s) of the test sample and the pattern of a control sample. A statistically significant difference can be determined by any test known to the person skilled in the art. Common tests for statistical significance include, among others, t-test, ANOVA1 Kruskal-Wallis, Wilcoxon, Mann-Whitney and odds ratio. Individual samples (of unknown status) can be compared with negative control samples obtained from subjects who are not afflicted with MS. A statistically significant elevation or reduction in the particular response parameter being measured between the test and control sample qualifies as a significant difference. A set of control samples can be stored as a reference collection for multiple analyses. In additional embodiments, where determining the subtype of MS is desired, the unknown test sample may be compared to a sample obtained from a subject known to be affricated with MS (positive control). In accordance with these embodiments, a significantly different response pattern of the test sample might be detected when the test sample of a subject with primary progressive multiple sclerosis (PPMS) is compared to a control sample of a subject with steady-state MS and vice versa.

The method of the present invention may further comprise the step of concentrating the test exhaled breath sample prior to the measurement using a breath concentrator and/or a dehumidifying unit.

Breath pre-concentrators that are within the scope of the present invention include, but are not limited to, I. Solid Phase Microextraction (SPME)—The SPME technique is based on a fiber coated with a liquid (polymer), a solid (sorbent), or combination thereof. The fiber coating extracts the compounds from the sample either by absorption (where the coating is liquid) or by adsorption (where the coating is solid). The SPME fiber is then inserted directly into the sensing apparatus for desorption and subsequent analysis (Ouyang, et al., Anal. Bioanal. Chem., 386, 1059-1073, 2006; Coelho et al., J. Chromatography B, 853, 1-9, 2007).

II. Sorbent Tubes—Sorbent tubes are typically composed of glass and contain various types of solid adsorbent material (sorbents). Commonly used sorbents include activated charcoal, silica gel, and organic porous polymers such as Tenax and Amberlite XAD resins. Sorbent tubes are attached to air sampling pumps for sample collection. A pump with a calibrated flow rate in ml/min draws a predetermined volume of air through the sorbent tube. Chemicals are trapped onto the sorbent material throughout the sampling period. This technique was developed by the US National Institute for Occupational Safety and Health (NIOSH).

III. Cryogenic Condensates—Cryogenic condensation is a process that allows recovery of volatile compounds for reuse. The condensation process requires very low temperatures so that the volatile compounds can be condensed. Traditionally, chlorofluorocarbon (CFC) refrigerants were used to induce condensation. Currently, liquid nitrogen is used in the cryogenic (less than −160° C.) condensation process.

A dehumidifier unit that is within the scope of the present invention includes, but is not limited to, I. A device which draws moist air over cold refrigerated coils—using this approach, the air moisture condenses into droplets as it passes through cold refrigerated coils into a container. "Dried" air is then brought to its original temperature and returned to the sensing apparatus.

II. Silica Gel—is an amorphous form of silicon dioxide, which is synthetically produced in the form of hard irregular granules or beads. A microporous structure of interlocking cavities gives a very high surface area (800 square meters per gram). This unique structure renders the silica gel as a high capacity desiccant. Water molecules adhere to the surface of the silica gel due to its low vapor pressure as compared to the surrounding air. When pressure equilibrium is reached, the adsorption ceases. Thus, the higher the humidity of the surrounding air, the larger the amount of water that is adsorbed before equilibrium is reached. Silica gel is advantageous as a drying substance since the process of drying requires no chemical reaction and it produces no by products or side effects.

III. Activated carbon—is formed by processing charcoal to an extremely porous carbon substance. Due to its high degree of microporosity, the activated carbon possesses a very large surface area available for chemical reactions. Sufficient activation may be obtained solely from the high surface area, though further chemical treatments often enhance the adsorbing properties of the material.

IV. Desiccant Molecular Sieves—are synthetically produced, highly porous crystalline metal-alumino silicates. They are classified by the many internal cavities of precise diameters, namely, 3 Å, 4 Å, 5 Å, and 10 Å. Adsorption occurs only when molecules to be adsorbed have smaller diameters than the cavity openings. Molecules of high polarity are better adsorbed into the molecular sieves. Molecular sieves adsorb water molecules and other contaminants from liquids and gases down to very low levels of concentrations, often to 1 ppm.

The method of the present invention enables the detection of a single volatile biomarker as well as the detection of a plurality of volatile biomarkers and the unique pattern of these biomarkers which characterizes a particular subtype or stage of MS. In certain embodiments, the volatile biomarker which is indicative of MS includes, but is not limited to, at least one of hexanal and 5-methyl-undecane. Each possibility represents a separate embodiment of the present invention. In one embodiment, the volatile biomarker which is indicative of MS is other than pentane.

The present invention encompasses the detection of breath biomarkers indicative of progressive multiple sclerosis (PMS) as well as breath biomarkers which are indicative of steady-state MS. Thus, according to the principles of the present invention, the discrimination between populations of healthy subjects, subjects having primary progressive multiple sclerosis (PPMS) and subjects having secondary progressive multiple sclerosis (SPMS) is afforded by the present invention. In addition, the present invention further provides the discrimination between healthy subjects, subjects in a relapsing remitting stage of multiple sclerosis (RRMS) and subject in a progressive stage of multiple sclerosis (PMS), which may be a primary progressive stage (PPMS) or secondary progressive stage (SPMS). In addition, the present invention further provides the discrimination between RRMS at remission and at a state of relapse (increased disease activity).

As used herein and in the appended claims the singular forms "a", "an," and "the" include plural references unless the content clearly dictates otherwise. Thus, for example, reference to "an organic coating" includes a plurality of such organic coatings and equivalents thereof known to those skilled in the art, and so forth. It should be noted that the term "and" or the term "or" is generally employed in its sense including "and/or" unless the content clearly dictates otherwise.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Example 1

Study design, Test Population and Breath Collection

Subjects who participated in this study were recruited from the MS patient population of the Carmel Medical Center, Haifa, Israel. The subjects fulfilled the MS clinical criteria of McDonald. Control subjects were recruited from MS patients' escorts to the clinic (unrelated spouse or acquaintance). The healthy control subjects are not afflicted with MS or any other autoimmune disease and were chosen to match the age and gender distribution of the MS subjects. The exclusion criteria from participating in the study comprised patients at the age of 18 or less, pregnant women, subjects afflicted with HIV, hepatitis or any other potentially severe and infectious disease, and healthy individuals with up to third degree relatives having MS or other autoimmune diseases.

Information regarding the subjects' personal and family medical history was collected via questionnaires as well as from medical records and supplementary forms filled by the treating doctors.

Based on the inclusion/exclusion criteria mentioned above, 51 volunteers were totally selected to participate in this study: 34 MS patients (24 presenting a steady state under the relapsing-remitting phase, 3 presenting a steady state under the progressive phase, and 7 presenting a relapsing stage under the relapsing-remitting phase) and 17 healthy subjects. The personal and clinical information regarding the subjects is summarized in Table 1.

TABLE 1

Personal and clinical information of the subjects who participated in this study

| No. | Clinical Classification of Subjects (Healthy/MS at Steady State/MS at Relapse Phase) | MS type (Relapsing-Remitting/Progressive) | Gender | Age | Smoking Habits | Food Additives | Other Chronic Disease | Pollution Exposure | Drug Treatment |
|---|---|---|---|---|---|---|---|---|---|
| 1 | MS Steady | RRMS | F | 38 | N | Y | N | N | Y |
| 2 | Healthy | — | M | 40 | Y | N | N | N | N |
| 3 | MS Steady | Unknown | F | 40 | N | Y | N | N | Y |
| 4 | Healthy | — | F | 24 | N | N | N | N | N |
| 5 | MS Relapse | RRMS | M | 24 | Y | Y | N | N | Y |
| 6 | MS Steady | PMS | F | 42 | N | Y | Depression | N | Y |
| 7 | MS Steady | RRMS | M | 42 | Y | N | No | N | Y |
| 8 | MS Steady | RRMS | M | 28 | Y | N | No | N | Y |
| 9 | MS Steady | Unknown | F | 50 | Y | N | No | N | N |
| 10 | MS Relapse | RRMS | F | 18 | N | Y | Asthma; migraine | N | Y |
| 11 | Healthy | — | F | 31 | Y | Y | No | N | N |
| 12 | MS Steady | RRMS | M | 63 | Y | Y | No | N | Y |
| 13 | Healthy | — | F | 30 | Y | N | No | N | N |
| 14 | MS Steady | RRMS | F | 40 | N | N | No | N | Y |
| 15 | MS Steady | RRMS | F | 28 | N | N | No | N | Y |
| 16 | MS Steady | RRMS | F | 47 | Y | Y | No | N | Y |
| 17 | MS Steady | RRMS | F | 60 | N | Y | wp Parkinson | N | Y |
| 18 | MS Steady | RRMS | F | 41 | N | Y | No | — | Y |
| 19 | MS Steady | RRMS | F | 43 | N | Y | No | N | Y |
| 20 | Healthy | — | F | 35 | N | Y | No | N | N |
| 21 | Healthy | — | F | 29 | N | N | No | N | N |
| 22 | MS Steady | RRMS | M | 45 | Y | Y | schizophrenia | Si | Y |
| 23 | Healthy | — | M | 35 | N | N | No | $NH_3$ Ni $H_2O_2$ | N |
| 24 | MS Steady | RRMS | F | 38 | N | Y | No | N | Y |
| 25 | MS Steady | RRMS | F | 25 | N | Y | No | N | Y |
| 26 | Healthy | — | F | 23 | N | Y | No | N | N |
| 27 | Healthy | — | F | 26 | N | N | No | N | Y |
| 28 | MS Steady | PMS | M | 39 | Y | Y | Chronic sinusitis | N | Y |
| 29 | MS Steady | RRMS | F | 52 | N | Y | Hypertension | N | Y |
| 30 | MS Steady | PMS | F | 46 | N | Y | Osteoporosis | N | Y |
| 31 | MS Steady | RRMS | M | 42 | Y | N | No | N | Y |
| 32 | MS Steady | RRMS | M | 59 | Y | N | No | N | Y |
| 33 | MS Steady | RRMS | M | 31 | N | N | No | N | Y |
| 34 | MS Relapse | Unknown | M | 23 | N | Y | No | Printing press | Y |
| 35 | MS Steady | RRMS | F | 45 | N | N | No | N | Y |
| 36 | Healthy | — | F | 49 | N.A. | — | — | — | — |
| 37 | MS Steady | RRMS | M | 46 | Y | N | No | N | Y |
| 38 | Healthy | — | M | 23 | N | N | No | N | N |
| 39 | Healthy | — | F | 25 | N | Y | Congenital adrenal hyperplasia | N | Y |
| 40 | MS Steady | RRMS | F | 49 | N | N | No | N | Y |
| 41 | MS Steady | RRMS | M | 49 | Y | N | No | N | Y |
| 42 | MS Steady | RRMS | F | 55 | N | N | No | N | Y |
| 43 | Healthy | — | M | 57 | Y | N | No | N | N |
| 44 | Healthy | — | M | 43 | N | N | No | N | Y |
| 45 | Healthy | — | F | 54 | Y | Y | No | N | Y |
| 46 | MS Relapse | RRMS | F | 43 | N | N | No | Chalk; Chlorine | Y |
| 47 | MS Relapse | RRMS | F | 50 | N | N | No | N | Y |
| 48 | Healthy | — | M | 54 | N | N | No | N | Y |
| 49 | MS Relapse | Unknown | F | 50 | N | Y | Arthritis; cholesterol | N | Y |
| 50 | Healthy | — | F | 37 | Y | N | No | N | N |
| 51 | MS Relapse | Unknown | M | 37 | Y | N | No | N | Y |

Alveolar breath of the subjects was collected using an 'offline' method that effectively separates the endogenous from the exogenous breath volatile biomarkers and excludes nasal entrainment. Two bags of 750 ml of breath samples per subject were collected in the MS center of Carmel Medical Center using an inert Mylar bags (Eco Medics, Duerten, Switzerland). Vapor sampling was performed by extended breath sampling into the collection apparatus for 15-20 minutes, with several stops during the process. The first three minutes of breath sampling were discarded due to the possible contamination of the upper respiratory air. The later deep air was retained for testing purposes. The samples were collected with a tube that was introduced into the subject's mouth and was connected to the collection bag.

All experiments were performed according to the guidelines of the Carmel Medical Center and Technion's Committee for supervision of human experiments, Haifa, Israel. All subjects had signed an informed consent. The clinical trial was approved by the Helsinki Committee of the Carmel Medical Center (#CMC 10-0003), and registered at ClinicalTrials.gov (registration no.:NCT01206023).

Additional breath samples were collected from other control groups including patients with autoimmune diseases other than MS, for example, patients having Insulin-Dependent Diabetes Mellitus (IDDM) and patients with other neurological diseases, such as patients having Parkinson's Disease (PD) and Parkinsonism, as well as Naïve MS patients prior to initiation of immunotherapy at steady state or exacerbation/relapse. Details of the personal and clinical information of the subjects are provided in Table 2.

TABLE 2

Personal and clinical information of patients with MS at different stages and control subjects

| Clinical classification | Female | Male | Average age | Female:Male ratio |
|---|---|---|---|---|
| Healthy control | 30 | 16 | 39 | 1.88 |
| IDDM control | 13 | 16 | 26 | 0.81 |
| PD control | 20 | 24 | 65 | 0.83 |
| Parkinsonism control | 9 | 8 | 67 | 1.12 |
| RRMS at steady state | 66 | 27 | 42 | 2.44 |
| RRMS at relapse | 5 | 9 | 35 | 0.55 |
| Naïve at steady state | 10 | 5 | — | 2 |
| Naïve at relapse | 2 | 2 | — | 1 |

Example 2

Sensor Breath Analysis

Breath samples were analyzed using the system of the present invention. Specifically, the system was composed of an array of 12 cross-reactive nanosensors based on organically functionalized gold nanoparticles and carbon nanotubes which were kept inside a ~300 ml sealed test chamber. The sensors and their organic coating are specified in Table 3. The details of the sensor fabrication process are described in Peng et al., Br. J. Cancer, 103, 542-551, 2010; and in Zilberman, et al., ACS NANO, 5(8), 6743-6753, 2011, the contents of which are hereby incorporated by reference in their entirety.

TABLE 3

Base materials and organic functionalities of the sensors. The sensors selected for performing each of the studies are indicated.

| Sensor No. | Base material | Organic functionality | Healthy-MS Patients | Steady State MS-Relapse Phase MS | Healthy-Steady State MS-Relapse Phase MS |
|---|---|---|---|---|---|
| 1 | GNP | Hexanethiol |  | X | X |
| 2 |  | Decanethiol #1[i] | X | X |  |
| 3 |  | Decanethiol #2[i] |  | X | X |
| 4 |  | Octadecanethiol | X | X |  |
| 5 |  | Tert-odecanethiol | X |  | X |
| 6 |  | 2-Mercaptobenzimidazole | X |  | X |
| 7 |  | 2-Ethylhexyl-3-Mercaptopropionate | X |  | X |
| 8 | CNT | PAH #1[ii] |  |  | X |
| 9 |  | PAH#2[iii] | X |  | X |
| 10 |  | PAH#3[iv] | X |  |  |
| 11 |  | PAH#4[v] | X |  |  |
| 12 |  | $C_{24}H_{50} + C_{24}H_{38}O_4$ |  | X |  |

[i]These sensors are not identical. They were differently fabricated and presented different reference values (the difference between their baseline resistances was 1 order of magnitude).
[ii]Polycyclic Aromatic Hydrocarbon derivative with an aromatic core of 42 carbons and hydrophobic mesogens terminated with ether.
[iii]Polycyclic Aromatic Hydrocarbon derivative with an aromatic core of 42 carbons and hydrophobic mesogens terminated with ester.
[iv]Polycyclic Aromatic Hydrocarbon derivative with an aromatic core of 42 carbons and hydrophobic mesogens terminated with alcohol.
[v]Polycyclic Aromatic Hydrocarbon derivative with a triangle-shaped core of 50 carbons and hydrophobic carbon chains.
GNP: Gold Nanoparticles;
CNT: Carbon Nanotubes.

The sensing measurements were performed as follows: before starting any new measurement, the sensors were kept in vacuum for 5 min in order to eliminate possible contaminations from the testing environment. The sensors were then exposed to a preset amount of a control analyte (10 ppm of isobutylene) for 5 min in order to indicate slight changes in sensors behavior due to normal aging and drift effects, followed by a new period of 5 min of vacuum in order to completely eliminate the control analyte from the testing environment. The content of one bag of breath sample was released inside the sensor system, being evacuated after 5 min, followed by a new period of 5 min of vacuum; finally, the content of the second bag of breath sample of the same subject was also released inside the sensor system, and the process of the first exposure was repeated in a similar manner. Sensors resistance was continuously acquired during the experiments. The relative humidity present in the breath samples was monitored using a humidity sensor which was placed inside the test chamber.

For each exposure (either to the control analyte or to each release of breath sample), three parameters were extracted from each sensor response as follows: normalized change of sensor resistance at the middle of the exposure and at the end of the exposure (referenced to the value of sensor resistance in vacuum prior to the exposure), and the area beneath the sensor resistance evolution curve during the last third section of the exposure period. In order to deduce information related to the response to volatile compounds solely, a compensation and calibration process was applied to the three parameters by subtracting the response of the sensors to the relative humidity present in the test chamber, and by dividing the obtained value with the corresponding value of the sensor response to the control analyte.

The mean values of the parameters thus obtained over the two successive exposures were used as inputs for a pattern recognition algorithm. Discriminant Factor Analysis (DFA) was employed to build predictive models for this study. DFA is a linear, supervised pattern recognition method in which the classes to be discriminated are defined before the analysis is performed. DFA determines the linear combinations of the input features such that the variance within each class is minimized and the variance between classes is maximized. The DFA output variables (i.e. canonical variables) are obtained in mutually orthogonal dimensions; the first canonical variable is the most powerful discriminating dimension, but the following canonical variables might also represent additional dimensions of differentiation. Thus, DFA effectively reduces the multidimensional experimental data, improves the human perception of the data and allows the distinction of clusters through visual perception of the first or the first and second canonical variables. Classification accuracy, sensitivity and specificity were estimated through leave-one-out cross-validation. Pattern recognition and data classification were conducted using the MATLAB® (MathWorks) environment.

Example 3

Breath Analysis Using Thermal Desorption Gas Chromatography Coupled with Mass Spectrometry (TDGC-MS)

Gas-Chromatography/Mass-Spectrometry (GCMS-QP2010; Shimadzu Corporation), combined with a thermal desorption system (TD20; Shimadzu Corporation) was used for chemical analysis of the tested breath. A Tenax TA tube (purchased from Sigma-Aldrich) was used for pre-concentrating the volatile compounds of the breath samples. Tube was mounted on a custom made pump apparatus for sample collection from the Mylar bag to the tube with a flow of 100 ml/min. Sample was further transferred to a TD tube (purchased from Sigma-Aldrich) for analysis on the TDGC-MS. The oven temperature profile was: 35° C., 10 min, 4° C./min to 150° C., 10° C./min to 300° C., 300° C., 15 min. Capillary column SLB-5ms 5% phenyl methyl siloxane (30 m length, 0.25 mm i.d., 0.5 µm thickness) was used (purchased from Sigma-Aldrich). Splitless injection mode for 2 min was used with a constant linear velocity of 30.0 cm/sec, and column flow of 0.70 ml/min. The identification of the volatile compounds was performed using the standard modular set. A 10 ppm isobutylene calibration gas (Calgaz, Cambridge, Md., USA) was used as a standard in each run, GC-MS chromatogram analysis was performed using the GC-MS postrun analysis program, GC-MS solutions version 2.53SU1 (Shimadzu Corporation) using National Institute of Standards and Technology (NIST) compound library (Gaithersburg, Md. 20899-1070 USA). Statistical test was performed by JMP, Version 9.0.0 (SAS Institute Inc., Cary, N.C., USA, 1989-2005).

Results

Identification of MS Using the System of the Present Invention

Figure 1:
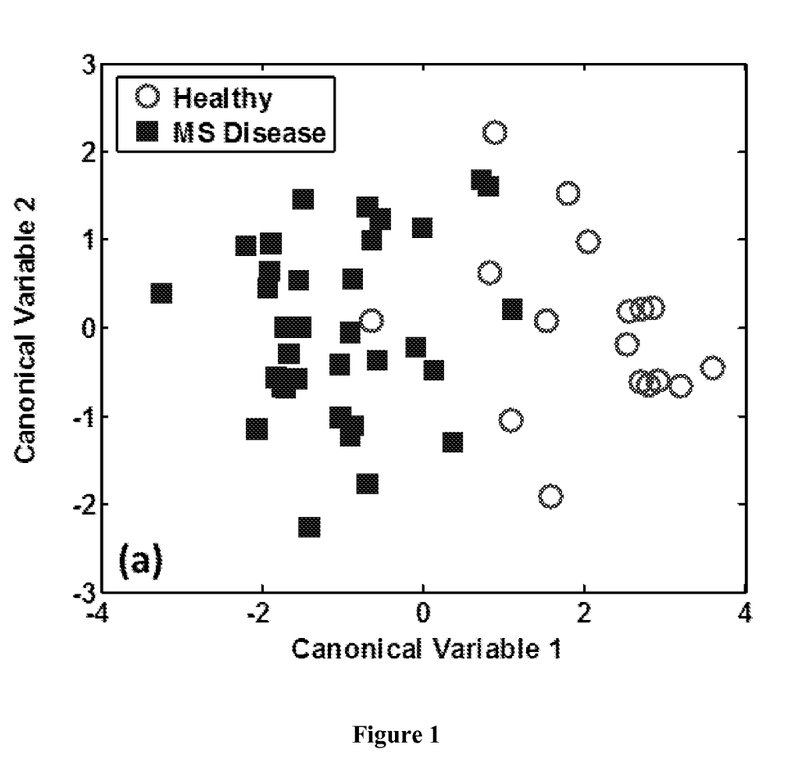
FIG. 1. DFA plot of the first two canonical variables of responses obtained from breath samples of healthy subjects (○) and MS patients (■).

An analysis of the breath samples of 34 patients with MS and 17 healthy controls (Table 1) using the system of the present invention was performed. FIG. 1 shows the DFA plot obtained from the responses of eight nanosensors (Table 3, Example 2). The classification success rate is summarized in Table 4. The sensitivity, specificity and accuracy of identifying MS were found to be 82.4, 88.2 and 84.3%, respectively. The accuracy of the system of the present invention in diagnosing MS is at the upper limit of the currently used method based on biomarkers' detection (75-85% employing electrophoresis). Thus, the values which are obtained using the system of the present invention fulfill the criteria for a good diagnostic method. The system of the present invention therefore provides the diagnosis of MS disease.

In order to verify the results, sample classifications based on different possible confounding factors (e.g. smoking habits and gender) were also performed. The accuracy of classifying smoking subjects was 48%, and the accuracy of classifying male subjects was 43.1%. The results of these classifications (summarized in Table 4) confirm that the system of the present invention is exclusively sensitive to exhaled breath biomarkers which are related to MS.

TABLE 4

Statistical classification

| Statistical Parameter | MS vs. Healthy | Smoking vs. Non-Smoking | Male vs. Female | Relapse vs. Steady | Healthy vs. Steady States vs. Relapse Phases | | |
|---|---|---|---|---|---|---|---|
| | | | | | Healthy | Steady State | Relapse Phase |
| Accuracy (%) | 84.3 | 48.0 | 43.1 | 91.2 | | 68.6 | |
| Sensitivity (%) | 82.4 | 42.1 | 36.8 | 85.7 | 70.6 | 70.4 | 57.1 |
| Specificity (%) | 88.2 | 51.6 | 46.9 | 92.6 | 82.1 | 84.2 | 79.5 |

Figure 2:
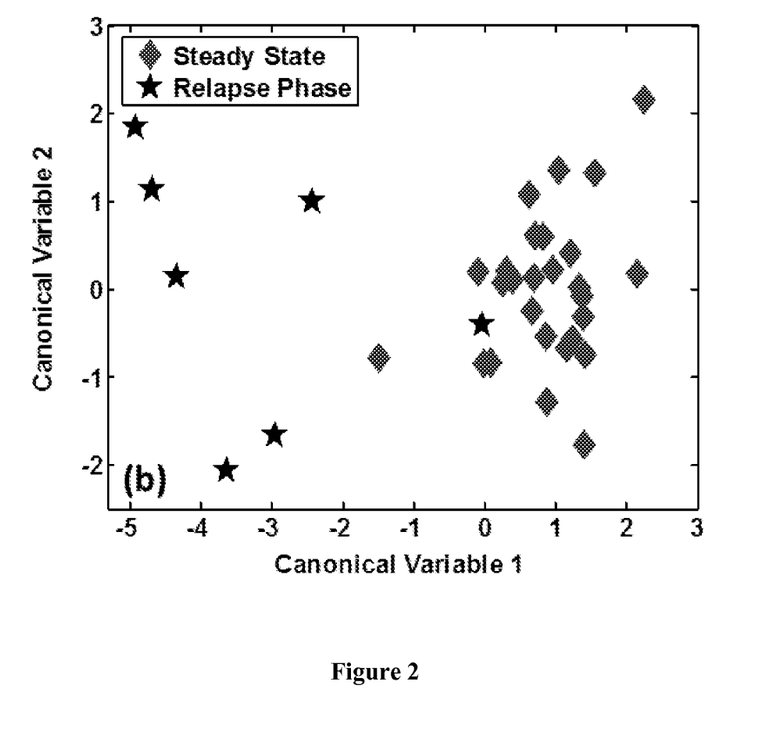
FIG. 2. DFA plot of the first two canonical variables of responses obtained from breath samples of MS patients in steady states (♦) and in relapse phases (★).

Classification of Different Subtypes of MS Using the System of the Present Invention An analysis of breath samples of MS patients (Table 1) was performed. 27 subjects having MS at steady state were compared to 7 subjects at relapse phase. The DFA plot obtained from the responses of five nanosensors (Table 3, Example 2) is shown in FIG. 2. The classification success rate is summarized in Table 4. The system of the present invention identified with very high accuracy (91.2%) MS patients at relapse phase. Very high sensitivity and specificity were also obtained (85.7 and 92.6%, respectively).

Figure 3:
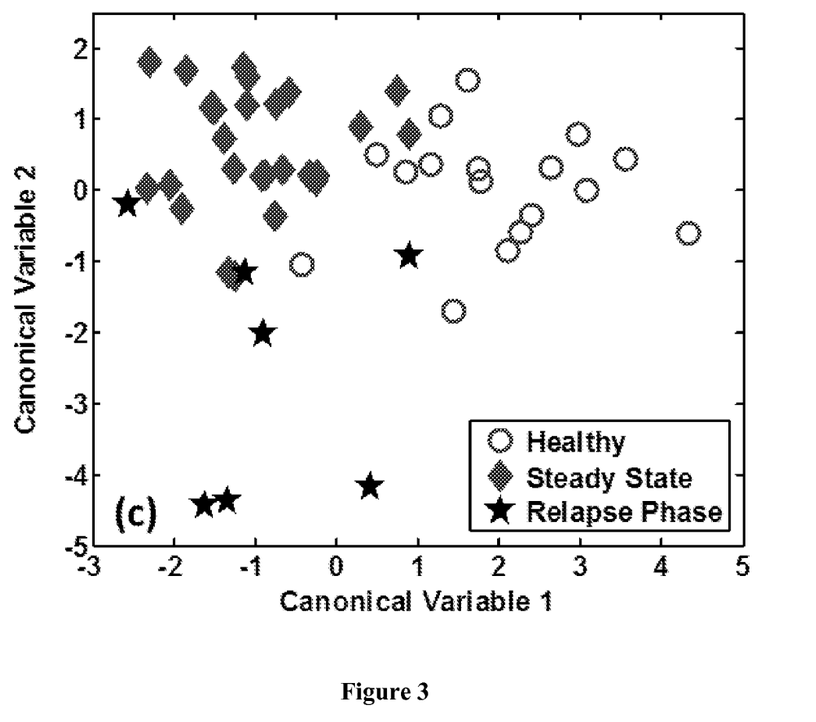
FIG. 3. DFA plot of the first two canonical variables of responses obtained from breath samples of healthy subjects (○), MS patients in steady states (♦) and MS patients in relapse phases (★).

In order to simultaneously discriminate between healthy controls, MS patients at steady state and MS patients at relapse phase, a further analysis was performed. The DFA plot obtained from the responses of seven nanosensors (Table 3, Example 2) is shown in FIG. 3. The sensitivity and specificity of estimating each one of the three sub-categories of populations is summarized in Table 4. Good results were obtained for estimating healthy and MS patients at steady state, while lower sensitivity was obtained for MS patients at relapse phase. Without being bound by any theory or mechanism of action, the lower sensitivity might be attributed to the relatively small subject population that was used in the analysis of this sub-category as compared with the populations of the two other sub-categories. Thus, the system of the present invention provides the classification of different subtypes of MS.

Identification of Volatile MS Biomarkers in Exhaled Breath

The chemical composition of the exhaled breath of MS patients was analyzed and compared to the breath of healthy controls in order to glean information regarding the volatile biomarkers which are indicative of MS. Each chromatogram resulted in hundreds of peaks. 214 potential peaks were further investigated in all test samples. The relative abundance was calculated based on the internal standard. Both parametric test assuming normal distribution of the data (student t-test) and non-parametric test assuming data which is not normally distributed (Wilcoxon test) were used to evaluate significant differences.

Two compounds showed small yet significant difference in the t-test while only one showed significant difference in the Wilcoxon test as summarized in Table 5 hereinbelow.

TABLE 5

Compounds that showed significant difference between healthy and MS populations

| # | m/z | Retention time [s] | p-value student t-test | p-value Wilcoxon test | compound identification |
|---|-----|--------------------|-----------------------|----------------------|------------------------|
| 1 | 44  | 14.657             | 0.0362                | 0.2034 (ns)*         | Hexanal                |
| 2 | 43  | 30.171             | 0.0353                | 0.0330               | 5-Methyl-Undecane      |

*ns—non-significant

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

The invention claimed is:

1. A method of diagnosing, monitoring or prognosing Multiple Sclerosis or stages thereof in a subject, the method comprising the steps of:

(a) providing a system comprising an apparatus comprising at least one sensor comprising nanomaterials selected from single walled carbon nanotubes coated with a first organic coating, metal nanoparticles coated with a second organic coating and a combination thereof, wherein the at least one sensor senses at least one volatile biomarker indicative of Multiple Sclerosis or stages thereof through adsorption of the biomarker on the nanomaterials; a detection means; and a processing unit comprising a pattern recognition analyzer comprising at least one pattern recognition algorithm;

(b) exposing the at least one sensor to a test exhaled breath sample;

(c) measuring at least one response induced parameter from the at least one sensor upon exposure to the test sample to obtain a response pattern; and (d) analyzing the response pattern obtained in step (c) using a pattern recognition algorithm by comparing it to stored data obtained from a control sample whereby a significantly different response pattern of the test sample as compared the control sample is indicative of Multiple Sclerosis or stages thereof.

2. The method according to claim 1, wherein the response pattern enables to differentiate between healthy subjects, subjects having primary progressive multiple sclerosis (PPMS), and subjects having secondary progressive multiple sclerosis (SPMS); or wherein the response pattern enables to differentiate between healthy subjects, subjects in a relapsing remitting stage of multiple sclerosis (RRMS) and subject in a progressive stage of multiple sclerosis (PMS); or wherein the response pattern enables to differentiate between subjects in a relapsing remitting stage of multiple sclerosis (RRMS) at remission and subjects in a relapsing remitting stage of multiple sclerosis (RRMS) at a state of relapse.

3. The method according to claim 1, for prognosing or monitoring the treatment of Multiple Sclerosis, or predicting a patient's response to a treatment regimen.

4. The method according to claim 1, for monitoring or predicting the course of the disease.

5. The method according to claim 1, further comprising the step of concentrating the test exhaled breath sample prior to step (b) using at least one of a breath concentrator and a dehumidifying unit.

6. The method according to claim 1, wherein the response pattern is formed by the sensor detecting the at least one volatile biomarker indicative of Multiple Sclerosis or stages thereof.

7. The method according to claim 1, wherein the first organic coating comprises small molecules, oligomers, polymers, or a combination thereof.

8. The method according to claim 7, wherein the first organic coating comprises compounds selected from propyl gallate ($C_{10}H_{12}O_5$), anthracene ($C_{14}H_{10}$), tetracosanoic acid ($C_{24}H_{48}O_2$), tricosane ($C_{23}H_{48}$), 3-methyl-2-phenyl valeric acid ($C_{12}H_{16}O_2$), tris(hydroxymethyl)nitro-methane ($C_4H_9NO_5$), tetracosane ($C24H_{50}$), dioctyl phthalate ($C_{24}H_{38}O_4$), 1,2,5,6,9,10-hexabrormo-cyclododecane ($C_{12}H_{18}Br_6$), pentadecane ($C_{15}H_{32}$), and combinations thereof; or wherein the first organic coating comprises hexa-peri-hexabenzocoronene (HBC) molecules which are unsubstituted or substituted by any one of 2-ethyl-hexyl (HBC-$C_{6,2}$), 2-hexyldecane (HBC-$C_{10,6}$), 2-decyl tetradecane (HBC-$C_{14,10}$), and dodecane (HBC-$C_{12}$).

9. The method according to claim 7, wherein the first organic coating comprises arenes, polyarenes or combinations thereof.

10. The method according to claim 9, wherein the arenes or polyarenes are selected from naphthalene, acenaphtene, anthracene, phenanthrene, pyrene, benzo[a]pyrene, chrysene, fluoranthene, $C_{18}$-$C_{180}$ graphenes and combinations thereof or wherein the arenes or polyarenes are substituted with one or more hydrophobic or hydrophilic carbon chains or at least one functional group selected from ester, ether, alcohol, amine, imine, amide, ammonium, keto, aldehyde, halogen (halo), pyridyl, phosphate, thiol, sulfonate, sulfonyl, hydroxyl, carboxylate, carboxyl, and carbonate groups.

11. The method according to claim 1, wherein the single walled carbon nanotubes are organized in a random network configuration.

12. The method according to claim 1, wherein the metal nanoparticles are selected from the group consisting of Au, Ag, Ni, Co, Pt, Pd, Cu, Al nanoparticles and combinations thereof.

13. The method according to claim 1, wherein the apparatus comprises a combination of a sensor comprising a plurality of single walled carbon nanotubes coated with a first organic coating and a sensor comprising a plurality of metal nanoparticles coated with a second organic coating, wherein the combination of sensors senses the at least one volatile biomarker indicative of Multiple Sclerosis or stages thereof through adsorption of the biomarker on the single walled carbon nanotubes and on the metal nanoparticles.

14. The method according to claim 1, wherein the metal nanoparticles have a morphology selected from a cubic, a spherical, and a spheroidal morphology.

15. The method according to claim 1, wherein the at least one sensor is configured in a form selected from the group consisting of a capacitive sensor, a resistive sensor, a chemiresistive sensor, an impedance sensor, and a field effect transistor sensor.

16. The method according to claim 1, wherein the detection means comprises a device for measuring changes in resistance, conductance, alternating current (AC), frequency, capacitance, impedance, inductance, mobility, electrical potential, optical property or voltage threshold.

17. The method according to claim 1, wherein the pattern recognition analyzer comprises at least one algorithm selected from the group consisting of artificial neural network algorithms, principal component analysis (PCA), multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART), partial least squares (PLS), multiple linear regression (MLR), principal component regression (PCR), discriminant function analysis (DFA), linear discriminant analysis (LDA), cluster analysis, and nearest neighbor.

18. The method according to claim 1, wherein the apparatus does not include a signaling agent.

19. A method of diagnosing, monitoring or prognosing Multiple Sclerosis or stages thereof in a subject, the method comprising the steps of:

(a) providing a system comprising an apparatus comprising at least one sensor comprising nanomaterials selected from single walled carbon nanotubes coated with a first organic coating, metal nanoparticles coated with a second organic coating and a combination thereof; a detection means; and a processing unit comprising a pattern recognition analyzer comprising at least one pattern recognition algorithm;

(b) exposing the at least one sensor to a test exhaled breath sample;

(c) measuring at least one response induced parameter from the at least one sensor upon exposure to the test sample to obtain a response pattern, wherein the response pattern is formed by the sensor detecting at least one volatile biomarker indicative of Multiple Sclerosis or stages thereof, the biomarker comprising hexanal or 5-methyl-undecane; and (d) analyzing the response pattern obtained in step (c) using a pattern recognition algorithm by comparing it to stored data obtained from a control sample whereby a significantly different response pattern of the test sample as compared the control sample is indicative of Multiple Sclerosis or stages thereof.

20. A method of diagnosing, monitoring or prognosing Multiple Sclerosis or stages thereof in a subject, the method comprising the steps of:

(a) providing a system comprising an apparatus comprising at least one sensor comprising nanomaterials selected from single walled carbon nanotubes coated with a first organic coating, metal nanoparticles coated with a second organic coating and a combination thereof, wherein the second organic coating comprises compounds selected from the group consisting of alkylthiols, arylthiols, alkylarylthiols, alkylthiolates, ω-functionalized alkanethiolates, arenethiolates, (γ-mercaptopropyl)tri-methyloxysilane, dialkyl disulfides and combinations and derivatives thereof; or wherein the second organic coating comprises compounds selected from the group consisting of hexanethiol, decanethiol, octadecanethiol, tert-odecanethiol, 2-mercaptobenzimidazole, 2-ethylhexyl-3-mercaptopropionate and combinations thereof; a detection means; and a processing unit comprising a pattern recognition analyzer comprising at least one pattern recognition algorithm;

(b) exposing the at least one sensor to a test exhaled breath sample;

(c) measuring at least one response induced parameter from the at least one sensor upon exposure to the test sample to obtain a response pattern; and (d) analyzing the response pattern obtained in step (c) using a pattern recognition algorithm by comparing it to stored data obtained from a control sample whereby a significantly different response pattern of the test sample as compared the control sample is indicative of Multiple Sclerosis or stages thereof.

* * * * *